United States Patent [19]

Kross

[11] Patent Number: 5,597,561
[45] Date of Patent: Jan. 28, 1997

[54] ADHERENT DISINFECTING COMPOSITIONS AND METHODS OF USE IN SKIN DISINFECTION

[75] Inventor: Robert D. Kross, Bellmore, N.Y.

[73] Assignee: Alcide Corporation, Redmond, Wash.

[21] Appl. No.: 356,067

[22] Filed: Dec. 14, 1994

[51] Int. Cl.$^6$ ............................ A61K 31/74; A61K 33/14
[52] U.S. Cl. .................................. 424/78.07; 424/78.02; 424/661; 424/665
[58] Field of Search .............................. 424/78.07, 78.02, 424/661, 665

[56] References Cited

U.S. PATENT DOCUMENTS

| | | | |
|---|---|---|---|
| Re. 31,779 | 12/1984 | Alliger | 252/187 |
| 4,330,531 | 5/1982 | Alliger | 424/149 |
| 4,891,216 | 1/1990 | Kross et al. | 424/661 |
| 4,956,184 | 9/1990 | Kross | 424/661 |
| 4,986,990 | 1/1991 | Davidson et al. | 424/665 |
| 5,100,652 | 3/1992 | Kross et al. | 424/53 |
| 5,185,161 | 2/1993 | Davidson et al. | 424/665 |
| 5,384,134 | 1/1995 | Kross et al. | 424/661 |
| 5,407,656 | 4/1995 | Roozdar | 423/477 |

*Primary Examiner*—Shelley A. Dodson
*Attorney, Agent, or Firm*—Seed and Berry LLP

[57] ABSTRACT

Disinfecting compositions directed to the prevention of microbial infections are disclosed. The disinfecting compositions comprise a protic acid, a metal chlorite and a gelling agent which, when combined, provide an effective adherent matrix that acts as a disinfectant barrier for preventing transmission and propagation of microbial infections. The gelling agent includes at least 25% polyacrylamide. The compositions of this invention may be used as presurgical disinfectants or as antiseptics for wounds and injection, phlebotomy and catheter insertion sites.

26 Claims, No Drawings

5,597,561

ADHERENT DISINFECTING COMPOSITIONS AND METHODS OF USE IN SKIN DISINFECTION

TECHNICAL FIELD

This invention relates generally to disinfecting compositions for preventing microbial infections and, more particularly, to an adherent matrix for preventing the transfer of bacteria into areas of skin penetration, such as wounds, phlebotomy sites and surgical or other incisions.

BACKGROUND OF THE INVENTION

Bacterial pathogens present a threat to the health and safety of patients wherever an area of skin is penetrated. For example, such pathogens may be a hazard during surgical procedures. Without adequate disinfection of the incision site prior to surgery, surface microorganisms or "skin flora" may transfer into the incision during surgery, resulting in internal infections after closure of the incision. To prevent such infections, known as "septic infections," it is critical to disinfect the incision site prior to surgery with a disinfectant that possesses a high antimicrobial activity and a broad spectrum of action. Since surgical procedures can last for many hours, it is also important that the initial disinfection of the incision site provide antimicrobial activity for an extended period of time.

In the United States, the Food and Drug Administration requires that a presurgical skin disinfectant be capable of reducing the number of flora on dry skin areas, such as an abdomen, by at least 2.5 logs or to levels that are too low for reliable quantification (less than about 25 cfu/cm$_2$). On moist skin, such as inguinal areas, the disinfectant must reduce the initial bacterial population by a minimum of 3.2 logs (1.5×10$^3$ cfu/ml), and maintain this level of bacteriostasis for at least four hours.

Presently, two antimicrobial materials have the requisite antimicrobial activity and longevity for use as a presurgical disinfectant. Both chlorhexidine gluconate (sold, for example, under the trademark HIBICLENS) and iodophors (sold, for example, under the trademark BETADINE) can protect patients from septic infections. However, these products require double applications and extended scrubbing with intervening wiping in order to adequately reduce microbial counts. For example, HIBICLENS calls for two individual 2- to 3- minute skin scrubbings, each with fresh material, with the final scrub allowed to dry on the skin. Similarly, BETADINE requires two 4-minute scrubbings, with the final scrub also allowed to dry on the skin. This lengthy scrubbing and drying period increases the time required to prepare a patient for surgery. The use of these products is therefore very costly, tying up the operating theater and a staff of medical professionals for the duration of the disinfecting process.

A disinfecting system that can function more rapidly, and thus reduce skin disinfection times significantly, is the chlorous acid system as described in U.S. Pat. No. 4,986,990. In that system, chlorous acid is produced in an aqueous medium by mixing a metal chlorite with a protic acid. The chlorous acid then degrades to a series of cidal oxidants, including chlorine dioxide, which collectively form the active disinfecting system.

Chlorous acid compositions can retain their antimicrobial activity for an extended period of time in dilute aqueous solution. However, these compositions lose their disinfecting properties when the aqueous solvent evaporates. Upon evaporation of the solvent, the chlorite ion converts to the corresponding chlorous acid form (HClO$_2$) and then to solid, inert residues of chloride and chlorate salts as the gaseous ClO$_2$ evaporates. As a result, these compositions have an active life of only a few minutes if used for presurgical skin disinfection.

Film-forming polymers can be used to generate intact films that remain on the skin for many hours after application, and such films may provide a physical barrier against deposition of environmental microorganisms on the skin at surgical sites. However, the use of film-forming polymers has not resulted in prolonging antimicrobial activity to supplement the protection afforded by the physical barrier of the film. In addition, there are only a few gelling agents that are stable in both the chlorite component solution and the acidic chlorous acid disinfecting composition. To date, only a polysulfonic acid polymer has been used in conjunction with the chlorous acid system disclosed in U.S. Pat. No. 4,891,216. The resulting composition, however, was found to generate a final film that was too tacky to be aesthetically acceptable. Thus, in spite of the potential advantages associated with the use of the chlorous acid system for presurgical disinfection, the extended 4-hour bacteriostasis required by the FDA has yet to be been attained for this system.

Extended disinfection is similarly important for non-surgical skin openings. For example, in disinfecting wound sites, it is important in many situations to not only destroy all contaminating pathogenic organisms, but to protect the wounds from subsequent contamination by environmental pathogen carriers such as air and clothing. Bandaging of sites will offer some protection as a physical barrier to environmental contamination, but often bandaging materials are counterindicated (e.g., on burned skin areas). No currently available skin antiseptic can provide the needed long-term disinfection (e.g., disinfection for a clay or more).

The areas surrounding in-dwelling catheters represent additional sites where both initial antisepsis and continued protection from bacterial penetration, over many days, is a necessity. Initial disinfection with, for example, alcohol, iodophors or chlorhexidine prior to insertion of a catheter is usually effective, but the region around the insertion site and the incised tissue is susceptible to rapid growth of contaminating pathogens.

In a like manner, blood-drawing sites (i.e., in the elbow crease) can represent surface areas where bacterial invasion may occur. This is increasingly likely for frequent blood donors, or for those individuals from whom blood samples are often taken. Frequent transdermal penetration in these areas results in tissue scarring (overtly visible and otherwise), characterized by uneven skin surfaces harboring organisms which are difficult to reach and destroy. When such areas are subsequently penetrated during injections or for blood transfusion, small sections of contaminated tissue can be carried directly into the blood stream. In such cases the prior application to these surfaces of a topical antiseptic with protracted antimicrobial activity would help in destroying these poorly accessible organisms.

Accordingly, there is a need in the art for a presurgical skin disinfectant of high antimicrobial capacity that can be applied rapidly in a single application, and that retains its disinfecting properties over the extended time periods of some surgical procedures. There is a similar need in the art for a topical antiseptic for use on wounds and injection or insertion sites that maintains a high antimicrobial activity for extended periods. The present invention fulfills these needs, and provides further related advantages.

SUMMARY OF THE INVENTION

In brief, this invention is directed to adherent disinfecting compositions for preventing microbial infections, as well as methods related to the use thereof for disinfecting substrate surfaces, including the skin of warm-blooded animals. The disinfecting compositions comprise a protic acid, a metal chlorite, and a gelling agent of which at least about 25% by weight is polyacrylamide. Optionally, the disinfecting compositions may further comprise a non-gelling film-former, a humectant, a preservative and/or a dye.

In one embodiment, a composition of this invention is applied to the surface of skin to disinfect the surface prior to surgery. In another embodiment, the composition is applied to a wound site to disinfect the site and provide protection against subsequent contamination. In yet another embodiment the composition is applied to an injection or insertion site, such as a catheter or phlebotomy site, to disinfect the site and prevent the transfer of pathogens from the skin to the site.

These and other aspects of this invention will become evident upon reference to the following detailed description.

DETAILED DESCRIPTION OF THE INVENTION

This invention is generally directed to an adherent disinfecting composition suitable for protecting against microbial infection. The disinfecting composition is applied to a substrate surface where it forms an "adherent matrix," which is a film on the substrate surface that actively protects against microbial infection.

In the context of the present invention, the term "disinfecting composition" refers to a composition (prior to application to the substrate surface and the formation of the adherent matrix) comprising a protic acid, a metal chlorite and a gelling agent. The term "protic acid" is defined in greater detail below. The term "metal chlorite" refers to alkali metal chlorites and alkaline earth metal chlorites, and includes so-called "stabilized chlorine dioxide" products that contain an alkali metal chlorite or an alkaline earth metal chlorite. The term "gelling agent" refers to a composition which, when combined with the other components of the disinfecting composition, increases the gelatinous quality or viscosity of the disinfecting composition and/or the adherent matrix; the term "non-gelling film-former" refers to a composition which, when added to the disinfecting composition, increases the membranous or film-like character of the adherent matrix without affecting the viscosity of both the disinfecting composition and the adherent matrix; the term "humectant" refers to a composition added as a softening agent which retains or attracts moisture to the skin, aiding in skin hydration. The term "preservative" refers to a composition added to the protic acid component to prevent deterioration of the protic acid.

The disinfecting composition of this invention may be provided in multiple phases. In one embodiment, the disinfecting composition is provided in three phases: a "protic acid solution" (which is an aqueous protic acid composition), a metal chlorite (in the form of a powder or an aqueous solution) and a gelling agent. In a preferred embodiment, the disinfecting composition is provided in two phases. The first phase comprises the protic acid. This phase may be a protic acid solution or a "protic acid gel," which is an aqueous composition comprising a protic acid and gelling agent. The second phase comprises the metal chlorite. If the first phase does not contain all of the gelling agent in the disinfecting composition, the second phase may additionally comprise some or all of the gelling agent. An aqueous phase that contains both metal chlorite and gelling agent is referred to as a "metal chlorite gel." In this two-phase system, all of the gelling agent in the disinfecting composition is provided in one or both of the phases.

Regardless of the form in which the gelling agent is provided, the total amount of gelling agent in the disinfecting composition generally ranges from about 0.25% to about 3.0%, preferably from about 0.25% to about 2.0%, and more preferably from about 0.5% to about 1.5% by weight of the disinfecting composition. The amount of gelling agent may depend on the location of the surface subject to disinfection. For horizontal surfaces, by way of example, gelling agents are generally present in an amount ranging from about 0.5% to about 2.0% by weight of the disinfecting composition. For vertical surfaces, the amount of gelling agent typically ranges from about 0.75% to about 2.5% by weight of the disinfecting composition.

The gelling agent of this invention is chosen to provide exceptional stability and other beneficial properties to the disinfecting composition and adherent matrix, as well as to the alkaline metal chlorite gel. To this end, the gelling agent is stable for a long period of time in the alkaline metal chlorite gel, and for at least 8–24 hours in the acidic disinfecting composition. Thus, the gelling agent possesses the unusual property of maintaining its viscosity in both alkaline and acidic chlorite conditions. Most compounds commonly employed as gelling agents do not possess this property. For example, although polyacrylic acid polymers ("carbopols") will maintain their viscosity in the alkaline oxidizing environment of chlorite solutions, these polymers lose much of their viscosity when the alkaline system (associated with —COO$^-$Na$^+$ groups on the polymer) converts to acidic conditions after contact with the protic acid component. Similarly, polymers susceptible to oxidative cleavage are not stable in the disinfecting composition. As a result, polymers derived from sugars, such as carrageenan (a polygalactan), ethyl-, methyl-, hydroxyethyl-, methyl hydroxyethyl- and methyl hydroxypropyl-cellulose, guar gum (a galactose/mannose polymer) and many naturally occurring polymers do not provide the desired stability, despite the fact that such materials may maintain their viscosity under both acid and alkaline conditions. Synthetic polymers derived from poly(alkylene oxide) chains (e.g., polyethylene oxide family) are also subject to such oxidative degradation, and therefore do not confer the desired stability. While these and other polymers may be present in the disinfecting composition, the amount of such additional polymers is maintained at a level such that they do not significantly detract from the viscosity of the disinfecting composition and the adherence of the protective barrier. Preferably, such polymers are present only in the protic acid component.

Of the numerous gelling agents commercially available, it has surprisingly been found that, in addition to the polysulfonic acid disclosed in U.S. Pat. No. 4,891,216, only polyacrylamide is suitable in the practice of this invention. More specifically, the polyacrylamide of the present invention has the following formula:

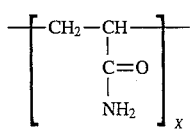

wherein X has a value such that the molecular weight is from about 1,000,000 to 20,000,000, preferably from about 2,500,000 to 10,000,000.

In the practice of this invention, between 25% and 100% of the gelling agent used to formulate the disinfecting composition must be polyacrylamide. Within this range, the amount of polyacrylamide may be varied, as described in more detail below, to alter the characteristics of the disinfecting composition and adherent matrix for specific applications. In a preferred embodiment, substantially all of the gelling agent that is not polyacrylamide is polysulfonic acid, or a suitable sulfonate salt thereof. The preparation of polysulfonates is disclosed and described in U.S. Pat. No. 4,891,216, which is incorporated herein by reference.

The protic acid component of the disinfecting composition may be any acid or mixture of acids capable of reducing the pH of the disinfecting composition to below about 6. Protic acids include organic acids, such as alpha-hydroxy acids of the general formula:

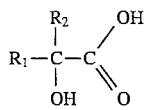

wherein $R_1$ and $R_2$ are independently selected from the group consisting of hydrogen, methyl, —$CH_2COOH$, —$CH_2OH$, —$CHOHCOOH$ and —$C_6H_5$. In a preferred embodiment, the protic acid is an organic acid having a pK ranging from about 2.8 to about 4.2, preferably from about 3.0 to about 4.0. Typical organic acids include citric, malic, tartaric, glycolic, lactic, and mandelic. Alternatively, the protic acid may be an inorganic acid having a pK ranging from about 0 to about 2.2, such as sulfuric, hydrochloric or phosphoric acid.

Those of ordinary skill in the art will recognize that the concentration of protic acid in the disinfecting composition will vary depending on the strength of the protic acid. Organic acids will generally be present in an amount ranging from 0.05% to about 5% by weight of the disinfecting composition. Stronger inorganic acids will generally be present in an amount ranging from about 0.005% to about 2% by weight of the disinfecting composition. In either case, the amount of protic acid in the disinfecting composition is sufficient to lower the pH of the disinfecting composition to below about 6, preferably from about 2 to about 5, and more preferably from about 2.5 to about 4.

In the practice of this invention, the protic acid may be provided as a protic acid solution or in the form of a protic acid gel, which is an aqueous composition that comprises a protic acid and a gelling agent. In either case, the amount of protic acid in the solution or gel is sufficient to render the pH of the protic acid solution or gel generally less than about 5.5, typically from about 2.0 to about 4.5, and preferably from about 2.2 to about 4.0.

In the case of a protic acid gel, the gelling agent comprises one or more components that increase the viscosity of the gel. The gelling agent is generally present in amounts up to 6.0%, typically from about 0.25% to about 3.0%, and preferably from about 0.5% to about 1.5% of the protic acid gel by weight. In a preferred embodiment, at least 50% of the gelling agent in the protic acid gel is polyacrylamide. More preferably, substantially all of the gelling agent in the protic acid gel is polyacrylamide.

Optionally, the protic acid solution additionally comprises one or more of the following: a non-gelling film-former, a humectant, a preservative and/or a dye. A non-gelling film-former is a polymer that dissolves in water and dries to a coherent film, but that does not interact with water molecules sufficiently for gelation to occur. While some gelling agents, such as polyacrylamide, form films as well as gels, a non-gelling film-former may be added to supplement the film provided by the gelling agent. Suitable non-gelling film-formers for supplementing the residual film provided by the gelling agent may be selected from those known in the art to be non-toxic and non-reactive (i.e., that do not react with chlorous acid or other components of the disinfecting composition). Non-gelling film-formers should also form clear solutions and should dry to films that are not tacky. Suitable non-gelling film-formers include polyvinyl alcohol (PVA), partially acetylated PVA, polyvinyl pyrrolidone, polyacrylic and methacrylic acids, and polyoxyethylene/propylene polymers and copolymers. Non-gelling film-formers may be added to the protic acid solution or gel in an amount dependent on the desired characteristics of the combined gel. Non-gelling film-formers may provide up to 3.0%, preferably from about 0.25% to about 2.0%, and more preferably from about 0.5% to about 1.5% by weight of the protic acid solution or gel.

The optional humectant portion of the protic acid solution or gel comprises any suitable humectant known in the art, including, by way of example, glycerin and sorbitol. A humectant is a hydrophilic material that holds and attracts moisture to the skin, aiding in skin hydration. Humectants generally comprise up to 5.0%, typically from about 0.2% to 2.0%, and preferably from about 0.4% to 0.8% by weight of the protic acid solution or gel.

The optional preservative portion of the protic acid solution or gel comprises any suitable preservative known in the art, including, by way of example, benzyl alcohol and sodium benzoate. Preservatives are generally present in an amount up to 0.08%, typically from about 0.01% to 0.06%, and preferably from about 0.02% to 0.04% by weight of the protic acid solution or gel. The optional dye may be any suitable dye known in the art, including by way of example, FD&C Yellow #5.

The metal chlorite component of the disinfecting composition may be any water-soluble chlorite. Typical water-soluble chlorites include alkali metal chlorites and alkaline earth metal chlorites. Sodium chlorite and potassium chlorite are preferred, and sodium chlorite is particularly preferred.

In the practice of this invention, chlorous acid and its cidal degradation products act as antimicrobial agents. The amount of chlorite ion that is in the form of chlorous acid varies depending on the pH of the composition. When the protic acid is an organic acid, with a pK greater than about 2.8, the metal chlorite is present in an amount such that no more than about 15% of the chlorite ion is in the form of chlorous acid. When the protic acid is a strong acid, with a pK lower than about 2.8, the metal chlorite may be used in an amount such that the amount of chlorite ion in the form of chlorous acid is no more than about 25% of the total chlorite ion.

To maintain the above chlorous acid concentration, the chlorite is present in the disinfecting composition in an amount ranging from about 0.01% to about 1.0% by weight. Preferably, the chlorite is present in an amount ranging from about 0.01% to about 0.45%, and more preferably from about 0.1% to about 0.35%, by weight of the disinfecting composition.

The metal chlorite may be provided in powder form, in an aqueous solution or in the form of a metal chlorite gel. In the case of a metal chlorite gel, the gelling agent comprises one or more compounds that increase the viscosity of the gel, and the gelling agent is generally present in amounts up to about 6.0%, preferably from about 0.25% to about 3.0%, and more preferably from about 0.5% to about 1.5% by weight of the metal chlorite gel. In a preferred embodiment, at least 15% of the gelling agent in the metal chlorite gel is polyacrylamide, and more preferably at least about 50% of the gelling agent in the metal chlorite gel is polyacrylamide.

Optionally, the metal chlorite component additionally comprises one or more of the following: a non-gelling film former, a humectant and/or a dye. Suitable non-gelling film-formers, humectants and dyes for use in the formulation of the metal chlorite gel are the same as described above in conjunction with the protic acid solution or gel.

The pH of the metal chlorite component should generally be maintained at greater than about 8, typically from about 8.5 to 12 and preferably from about 9 to 11. Suitable compounds for adjusting the pH of the metal chlorite gel will be apparent to those skilled in the art, and include sodium hydroxide.

By varying the amount and composition of the gelling agent and non-gelling film-formers, the characteristics of the disinfecting composition and adherent matrix formed therefrom may be varied according to the desired antimicrobial application. Characteristics which may be varied include: drying time, ease of removal with or without water, affinity to skin, viscosity, and membranous quality. In the practice of this invention, these characteristics are generally controlled by varying the amount and nature of gelling agent and the ratio of gelling agent to non-gelling film-formers.

For example, in some applications it may be advantageous to increase or decrease the viscosity of the disinfecting composition. The disinfecting composition will generally require a higher viscosity when the adherent matrix is to be formed on vertical surfaces, and often when extended antimicrobial or barrier properties are desired. In contrast, the disinfecting composition will generally require a lower viscosity when the adherent matrix is to be formed on horizontal surfaces, when gauze or cotton applicators are used, when faster evaporation is desired, and when there are nooks and crannies on the surface that must be filled.

For presurgical application, a lower viscosity in the range of about 5 cps to about 100 cps is generally appropriate. This slightly enhanced viscosity is generally sufficient to prevent run-off from the skin and to form a cohesive occlusive film that retains residual antimicrobial material, such as unreacted acid. For other applications, such as wounds on vertical skin surfaces, viscosities of about 50 cps to 500 cps are more appropriate.

For some applications, where extended antimicrobial activity is of particular importance, the composition may be formulated so as to entrap free acid within the adherent matrix. To provide sufficient free acid, the level of protic acid used in combination with the metal chlorite can be set such that there is a significant molar excess of such acid with respect to the level of chlorite salt. When the chlorite salt has been completely converted to its acid form, therefore, there will remain a discrete quantity of unconsumed free acid. The latter, when entrapped in the residual film from this disinfecting composition, provides extended antimicrobial activity to the film. Unlike other antimicrobial agents which might be entrapped in topical films, and which lose activity within hours of application, these acids will tend to remain in their active, free acid form by reaction with natural acidity supplied by the acid mantle on skin surfaces.

To prepare a disinfecting composition with a lower viscosity, the amount of gelling agent may be decreased. To maintain a cohesive film while decreasing the amount of gelling agent, the amount of non-gelling film-formers may be increased. The use of a low level of gelling agent (less than about 1%) will result in a product that leaves relatively low amounts of material on the substrate surface. In determining how much gelling agent should be used, one of ordinary skill in the art will appreciate that the molecular weights of the gelling agents may be taken into account. In other words, a lesser amount of a long-chain polymer may impart the same viscosity to a solution as a greater amount of a shorter-chain polymer.

For other applications it may be advantageous to increase or decrease the adherent affinity of the matrix to the skin. Generally, polysulfonic acid has a higher affinity for skin; polyacrylamide does not have as high an affinity for skin, but forms a more cohesive film and dries more fully. The affinity for skin is also a function of the amount and nature of non-gelling film-formers.

The ease with which the adherent matrix is removed with water may also be varied. Ease of removability is enhanced by increasing the amount of the polyacrylamide component. A preferred/formulation for presurgical application that will protect the site from microbial infection and yet be readily removed, includes a composition in which substantially all of the gelling agent in the disinfecting composition is polyacrylamide, where the total amount of gelling agent ranges from about 0.25% to about 1.5% by weight of the disinfecting composition.

It may also be advantageous to generate a disinfecting composition that dries rapidly. Drying time of the disinfecting composition is important when the length of time required to prepare the patient for surgery is of particular concern. It is also important when preparing sites for injection or transdermal insertion of a catheter. When altering this characteristic, temperature, which tends to enhance evaporation, and humidity, which tends to suppress evaporation and increase drying time in the absence of non-gelling film-formers and humectants, should be taken into account. In general, increasing the ratio of polyacrylamide to polysulfonic acid decreases the drying time. Typical ratios of polyacrylamide to polysulfbnic acid for rapidly drying disinfecting compositions range from about 1:1 to about 10:1, preferably from about 2:1 to about 5:1.

When the disinfecting composition of this invention is provided in two phases, the protic acid component and the metal chlorite component are mixed in suitable ratios to generate the chlorous acid, and the disinfecting composition is then applied to the surface to be disinfected. Preferably, the two phases are combined in approximately equal pans. More preferably, the disinfecting composition is mixed immediately prior to application.

An effective amount of the disinfecting composition for application to skin will vary. Generally, a sufficient amount will be that which reduces the microbial population by more than 3.2 logs per square centimeter of skin for a period of four hours. The application of about 0.1 to 4.0 grains to an area of about 1 to 10 square inches will typically afford antimicrobial barrier protection. The disinfecting composition is applied to the skin and allowed to dry on the skin surface to yield the adherent matrix.

The present invention is illustrated by the following examples, which are to be regarded as illustrative rather than restrictive. Unless otherwise noted, all parts and percentages in the examples, as well as the specification and claims, are by weight.

EXAMPLES

Example 1

This example illustrates the use of a representative disinfecting composition of the present invention as a skin disinfectant for use prior to surgery. The composition dries on the skin to form a protective adherent matrix after initial disinfection has taken place.

A protic acid gel is prepared by mixing the following ingredients:

| | |
|---|---|
| Malic acid | 2.00% |
| Polyacrylamide | 1.00% |
| Isopropyl alcohol | 25.0% |
| Sodium benzoate | 0.04% |
| Deionized water | q.s. |

A metal chlorite gel is prepared by mixing the following ingredients:

| | |
|---|---|
| Sodium chlorite | 0.80% |
| Polyacrylamide | 1.00% |
| Triton X-100 | 0.45% |
| Isopropyl alcohol | 25.0% |
| Deionized water | q.s. |

The two gels are blended in approximately equal amounts, preferably just prior to application. The resulting disinfecting composition has an initial pH of 3.0, and is rubbed onto the skin for 1–2 minutes. Upon drying, the disinfected area develops a protective adherent matrix which prevents foreign bacteria from recontaminating the skin.

Example 2

This example illustrates the use of a representative disinfecting composition of the present invention as a skin disinfectant for use prior to surgery, where the adherent matrix provides additional longer-lasting antimicrobial activity due to the nature and level of unconsumed acid activator.

A protic acid gel is prepared by mixing the following ingredients:

| | |
|---|---|
| Mandelic acid | 5.00% |
| Sulfuric acid, 1N | 2.00% |
| Polyacrylamide | 0.75% |
| Poloxamer 188 | 0.62% |
| Sodium benzoate | 0.04% |
| Isopropyl alcohol | 15.00% |
| Deionized water | q.s. |

A metal chlorite gel is prepared by mixing the following ingredients:

| | |
|---|---|
| Sodium chlorite | 1.00% |
| Polyacrylamide | 0.75% |
| Octylphenoxypolyoxyethylene (N = 12) | 0.45% |
| Polyethylene glycol 4600 | 0.30% |
| Isopropyl alcohol | 15.00% |
| Tetrasodium edetate | 0.19% |
| Deionized water | q.s. |

The adherent matrix resulting from application of a mixture of equal pans of both gels to the skin has an initial pH of 2.55 and contains mandelic acid, which further destroys skin organisms not initially killed by the chlorous acid in the mixed composition. This is shown in the data presented in Table 1 below, which summarizes the data derived from application of this composition to the inguinal area of five (5) patients. The data are the logarithmic (and numerical) reductions of total skin flora, in cfu/cm$^2$ of skin, as compared with untreated inguinal areas at 10 minutes, 30 minutes and 4 hours after application of the composition to the skin.

TABLE 1

| Logarithmic and Numerical Reduction of Inguinal Skin Microorganisms | |
|---|---|
| Time | Logarithmic (Numerical) Reduction |
| 10 minutes post application | 3.36 logs (2,290) |
| 30 minutes post application | 4.44 logs (27,540) |
| 4 hours post application | 5.17 logs (147,900) |

The data in Table 1 demonstrate that this disinfecting composition reduces the initial population of microorganisms by more than the FDA required 3.2 logs within 10 minutes of application, and that the composition retains its antimicrobial activity for at least 4 hours following application.

Example 3

This example illustrates the use of the disinfecting composition provided in Example 1 for reducing microbial levels on skin prior to insertion of an indwelling catheter or prior to an injection with a hypodermic syringe. Using a panel of 10 human subjects, the antimicrobial effectiveness was compared, over a 72-hour period, with that of a standard 10% Povidone Iodine Paint (1.0% available iodine) on four anatomical sites; subclavian vein, femoral vein, median cubital vein near the forearm, and the deltoid region (the latter only for a 30-second, injection-related application). The average log reductions (and standard deviations) found for each of the sites, as compared with baseline values on adjacent skin site, were as follows (standard deviations given parenthetically below each figure):

| | Time Interval | | | |
|---|---|---|---|---|
| Skin Site | 30 sec. | 24 hrs. | 48 hrs. | 72 hrs. |
| | log reduction vs. baseline | | | |
| DELTOID | | | | |
| Ex. 1 Formula | 1.85 | — | — | — |
| | (0.72) | — | — | — |
| Pov. Iodine | 1.42 | — | — | — |
| | (0.94) | — | — | — |
| FEMORAL VEIN | | | | |
| Ex. 1 Formula | 2.02 | 2.79 | 2.41 | 2.92 |
| | (1.46) | (2.01) | (1.67) | (1.80) |
| Pov. Iodine | 1.26 | 1.78 | 2.55 | 3.40 |
| | (0.90) | (1.39) | (1.71) | (2.26) |
| SUBCLAVIAN VEIN | | | | |
| Ex. 1 Formula | 2.02 | 1.22 | 1.95 | 2.03 |
| | (0.82) | (1.47) | (1.31) | (1.97) |
| Pov. Iodine | 1.46 | 1.20 | 0.77 | 1.63 |
| | (1.23) | (1.39) | (2.01) | (1.28) |
| MEDIAN CUBITAL | | | | |
| Ex. 1 Formula | 1.38 | 1.15 | 0.39 | −0.25 |
| | (0.61) | (0.98) | (1.99) | (1.63) |
| Pov. Iodine | 0.89 | 0.79 | 0.46 | 0.08 |
| | (1.47) | (1.62) | (1.46) | (1.88) |

It can be seen from these comparative data, that the composition provided in Example 1 is capable of immediately reducing, and then maintaining for about 72 hours, the microbial population on various skin sites where injections or catheter insertions may take place. The data compare favorably with a standard commercial product currently being used for a similar disinfection, where that product is recognized as a skin irritant, and is counter-indicated in a significant number of people.

From the foregoing, it will be evident that although specific embodiments of the invention have been described herein for the purpose of illustrating the invention, various modifications may be made without deviating from the spirit and scope of the invention.

I claim:

1. A composition for disinfecting a substrate and providing a protective anti-microbial barrier, comprising:
   (a) a protic acid;
   (b) a metal chlorite; and
   (c) a gelling agent in an amount ranging from about 0.25% to about 3.0% by weight of the composition, wherein the gelling agent comprises 25% to 100% by weight polyacrylamide.

2. The composition of claim 1 wherein the gelling agent is present in an amount ranging from about 0.25% to about 2.0% by weight of the composition.

3. The composition of claim 1 wherein the gelling agent is present in an amount ranging from about 0.5% to about 1.5% by weight of the composition.

4. The composition of claim 1 wherein the protic acid is an organic acid present in an amount ranging from about 0.05% to about 5% by weight of the composition.

5. The composition of claim 1 wherein the protic acid is an inorganic acid present in an amount ranging from about 0.005% to about 2% by weight of the composition.

6. The composition of claim 1 wherein the metal chlorite is present in an amount ranging from about 0.01% to about 1.0% by weight of the composition.

7. The composition of claim 1 wherein the polyacrylamide is present in the gelling agent in an amount ranging from 50% to 100% by weight.

8. The composition of claim 1 wherein the polyacrylamide has a molecular weight ranging from about 1,000,000 to about 20,000,000.

9. The composition of claim 1 wherein the polyacrylamide has a molecular weight ranging from about 2,500,000 to about 10,000,000.

10. The composition of claim 1 wherein substantially all of the gelling agent that is not polyacrylamide is polysulfonic acid.

11. A composition for disinfecting a substrate and providing a protective antimicrobial barrier, comprising a first and second phase adapted to be mixed and applied so as to adhere to the substrate, the first phase comprising a protic acid and the second phase comprising a metal chlorite, wherein one or both of the first and second phases additionally comprise a gelling agent such that the total amount of gelling agent ranges from about 0.25% to about 3.0% by weight of the composition, and wherein 25% to 100% by weight of the gelling agent is polyacrylamide.

12. The composition of claim 11 wherein the first phase comprises the gelling agent.

13. The composition of claim 11 wherein the second phase comprises the gelling agent.

14. The composition of claim 11 wherein the first and second phases comprise the gelling agent.

15. The composition of claim 11 wherein the gelling agent that is not polyacrylamide is polysulfonic acid.

16. The composition of claim 11 wherein the first phase comprises at least a portion of the gelling agent in an amount up to about 3.0% by weight of the first phase.

17. The composition of claim 11 wherein the first phase comprises at least a portion of the gelling agent in an amount ranging from about 0.5% to about 1.5% by weight of the first phase.

18. The composition of claim 11 wherein the second phase comprises at least a portion of the gelling agent in an amount up to about 3.0% by weight of the second phase.

19. The composition of claim 11 wherein the second phase comprises at least a portion of the gelling agent in an amount ranging from about 0.5% to about 1.5% by weight of the second phase.

20. A method for disinfecting a substrate comprising applying to the substrate an effective amount of a composition comprising:
   (a) a protic acid;
   (b) a metal chlorite; and
   (c) a gelling agent in an amount ranging from about 0.25% to about 3.0% by weight of the composition, wherein the gelling agent comprises 25% to 100% by weight polyacrylamide.

21. The method of claim 20 wherein the substrate is the skin of a warm-blooded animal.

22. The method of claim 21 wherein the substrate is a wound.

23. The method of claim 21 wherein the substrate is a region of skin being prepared for surgical incision.

24. The method of claim 21 wherein the substrate is a region of skin being prepared for phlebotomy.

25. The method of claim 21 wherein the substrate is a region of skin being prepared for insertion of a catheter.

26. The method of claim 20, further comprising the step of mixing a first phase and a second phase prior to applying the composition to the substrate, wherein the first phase comprises the protic acid and the second phase comprises the metal chlorite, and wherein the gelling agent is provided in one or both of the first and second phases.

* * * * *